(12) United States Patent
Pendergast et al.

(10) Patent No.: US 10,144,698 B2
(45) Date of Patent: Dec. 4, 2018

(54) BREAKING A METHANOL/METHYL METHACRYLATE AZEOTROPE USING PRESSURE SWING DISTILLATION

(71) Applicants: DOW GLOBAL TECHNOLOGIES LLC, Midland, MI (US); ROHM AND HAAS COMPANY, Philadelphia, PA (US)

(72) Inventors: John G. Pendergast, Pearland, TX (US); William G. Worley, Missouri City, TX (US); Stacy W. Hoy, IV, Houston, TX (US); Jacob M. Crosthwaite, Midland, MI (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 59 days.

(21) Appl. No.: 15/521,798

(22) PCT Filed: Oct. 2, 2015

(86) PCT No.: PCT/US2015/053663
§ 371 (c)(1),
(2) Date: Apr. 25, 2017

(87) PCT Pub. No.: WO2016/069198
PCT Pub. Date: May 6, 2016

(65) Prior Publication Data
US 2017/0247313 A1    Aug. 31, 2017

Related U.S. Application Data

(60) Provisional application No. 62/073,401, filed on Oct. 31, 2014.

(51) Int. Cl.
| | | |
|---|---|---|
| C07C 67/54 | (2006.01) | |
| C07C 29/82 | (2006.01) | |
| B01D 3/00 | (2006.01) | |
| B01D 3/14 | (2006.01) | |
| B01D 3/36 | (2006.01) | |

(52) U.S. Cl.
CPC .............. *C07C 67/54* (2013.01); *B01D 3/007* (2013.01); *B01D 3/143* (2013.01); *B01D 3/36* (2013.01); *C07C 29/82* (2013.01)

(58) Field of Classification Search
CPC ......... C07C 67/54; C07C 69/54; C07C 29/82; B01D 3/007; B01D 3/143; B01D 3/36
See application file for complete search history.

(56) References Cited

U.S. PATENT DOCUMENTS

| | | |
|---|---|---|
| 4,249,019 A | 2/1981 | Tamura et al. |
| 4,518,462 A | 5/1985 | Aoshima et al. |
| (Continued) | | |

OTHER PUBLICATIONS

Yi Chang Wu, et al., Ind. Eng. Chem. Res. 2011, 50, 4595-4607.

*Primary Examiner* — Renee Robinson
*Assistant Examiner* — Derek N Mueller
(74) *Attorney, Agent, or Firm* — Husch Blackwell LLP

(57) ABSTRACT

A methanol/MMA azeotrope is broken or avoided by a method comprising the steps of (1) raising the pressure within a first vessel, e.g., a distillation column, that contains a methanol/MMA azeotrope, (2) collecting the azeotrope as a liquid, and then in a second, separate vessel, e.g., another distillation column, (3) raising the pressure sufficiently to allow for the breaking of or avoidance of the azeotrope and the recovery of the methanol.

6 Claims, 2 Drawing Sheets

(56) References Cited

U.S. PATENT DOCUMENTS

| | | | |
|---|---|---|---|
| 4,518,796 | A | 5/1985 | Aoshima et al. |
| 4,937,302 | A | 6/1990 | Schoedel |
| 5,028,735 | A | 7/1991 | Segawa et al. |
| 5,435,892 | A | 7/1995 | Miyazaki et al. |
| 5,892,102 | A | 4/1999 | Mikami et al. |
| 5,969,178 | A | 10/1999 | Okamoto et al. |
| 6,040,472 | A | 3/2000 | Yamamatsu et al. |
| 6,107,515 | A | 8/2000 | Yamaguchi |
| 6,680,405 | B1 | 1/2004 | Munetou et al. |

BREAKING A METHANOL/METHYL METHACRYLATE AZEOTROPE USING PRESSURE SWING DISTILLATION

FIELD OF THE INVENTION

This invention relates to breaking a methanol/methyl methacrylate (MMA) azeotrope using pressure swing distillation. In one aspect the invention relates to the recovery and recycle of the methanol used in the manufacture of MMA.

BACKGROUND OF THE INVENTION

Methanol is used in the manufacture of methyl methacrylate (MMA). Methanol and MMA form an azeotrope or a "near azeotrope", otherwise known as a "tangent pinch". This means that there is no separation possible between the methanol and MMA without a means of breaking the azeotrope.

One method of breaking a methanol/MMA azeotrope is by changing the pressure in that part of the MMA manufacturing process containing the azeotrope. However, raising the pressure only results in shifting the vapor concentration slightly above the liquid concentration. Without further modifications to this arrangement, the energy penalty for this operation is prohibitive.

U.S. Pat. No. 4,937,302 teaches a method for the separation of technical methanol-MMA mixtures by polymerization of the MMA. The polymerization is suitably carried out as a copolymerization, at least with long-chain aliphatic $C_8$ to $C_{20}$-alkyl esters of methacrylic acid as comonomers, and as a solution polymerization, and the methanol is recovered by distillation.

German patent publication DE-OS No. 32 11 901 describes a method for the separation of methanol from aqueous mixtures of MMA and methanol, such as are formed in the esterification of methacrylic acid with methanol, in which are added to the mixture azeotrope-formers which, in the presence of MMA and water, form with methanol azeotropes which have a boiling point at least 0.2 Centigrade degrees below the boiling point of the azeotrope of methanol and MMA.

JP 03819419 B2 describes a methanol recovery column where the methanol and methacrolein are separated from MMA in a distillation column with no other separating agents added. The overhead composition is limited by the azeotropic composition (11 wt % of MMA in methanol). While the azeotropic composition can be approached by using a large number of trays and/or a high reflux ratio, the MMA composition in the overheads cannot be less than the azeotropic composition. This is undesirable as the MMA is the desired product, and sending it back to the reactor requires larger equipment and, more importantly, provides the opportunity for the valuable product to react further to by-products, thereby lowering the MMA yield.

U.S. Pat. No. 4,518,462 describes the removal of methanol from MMA using a $C_6$-$C_7$ saturated hydrocarbon, e.g. hexane, cyclohexane, heptane, methyl cyclopentane or dimethylpentane, as an entrainer. No water is added to the overheads decanter, so the phases split into hydrocarbon-rich and methanol-rich layers. One of the drawbacks of this approach is the limited ability to dry the recycle stream. In addition, in order to reduce the MMA to low levels in the recycle stream, a large amount of entrainer is required, resulting in high energy usage and a large and expensive distillation column.

U.S. Pat. Nos. 5,028,735, 5,435,892, and JP 02582127 B2 describe a similar entrainer process where either sufficient water is in the feed or water is added to the overhead decanter to form an organic and aqueous layer. In this case, essentially all of the hydrocarbon entrainer resides in the organic layer. The aqueous layer can be sent to a drying column to remove water from the recycle stream; however, large amounts of hexane are still required to minimize MMA in the recycle stream. For example, U.S. Pat. No. 5,028,735 describes an entrainer process using hexane as the entrainer with hexane usage of at least 17-fold the water content of the feed and 3-fold the methanol in the feed.

U.S. Pat. No. 6,680,405, uses methacrolein as an entrainer. While the azeotrope composition was broken, it resulted in only a minor improvement, namely 7.4% MMA in the recycle stream.

SUMMARY OF THE INVENTION

In one embodiment of this invention, a methanol/MMA azeotrope is broken or avoided by a method comprising the steps of (1) raising the pressure within a first vessel, e.g., a distillation column, that contains a methanol/MMA azeotrope, (2) collecting the azeotrope as a liquid, and then in a second, separate vessel, e.g., another distillation column, (3) raising the pressure sufficiently to allow for the recovery of the methanol. In one embodiment of the invention, the process is conducted without the use of an azeotropic agent. In one embodiment of the invention, the process is conducted with the use of an azeotropic agent.

In one embodiment of the invention, the lower pressure vessel, i.e., the first vessel, is equipped with a reboiler, and the higher pressure vessel, i.e., the second vessel, acts as a heat pump for the reboiler of the lower pressure vessel thus reducing the energy consumption required to operate the lower pressure vessel.

In one embodiment the invention is a process for breaking or minimizing a methanol/methyl methacrylate (MMA) azeotrope, the process comprising the steps of:

(A) Feeding a liquid stream comprising methanol and MMA to a first distillation column operated at a first pressure and equipped with a reboiler;

(B) Separating the liquid stream within the first distillation column into a first distillation column overheads stream comprising a methanol/MMA azeotrope and a first distillation column bottoms stream;

(C) Transferring the first distillation column overheads stream to a second distillation column operated at a second pressure, the operating pressure of the second distillation column greater than the operating pressure of the first distillation column;

(D) Separating the first distillation column overheads stream within the second distillation column into a second distillation column overheads stream comprising an amount of methanol/MMA azeotrope that is less than the amount of methanol/MMA azeotrope in the first column overheads stream, and a second distillation column bottoms stream; and (E) Recovering at least a part of the second distillation column overheads stream.

In one embodiment the methanol and MMA are within a product stream of an MMA manufacturing process in which methacrylic acid and methanol are reacted. In one embodiment the process comprises the further step of recycling at least a part of the second distillation column overheads stream to the reboiler of the first distillation column. In one embodiment the process employs the use of an azeotropic agent. In one embodiment the process does not employ the use of an azeotropic agent.

DETAILED DESCRIPTION OF THE PREFERRED EMBODIMENT

Definitions

Figure 1:
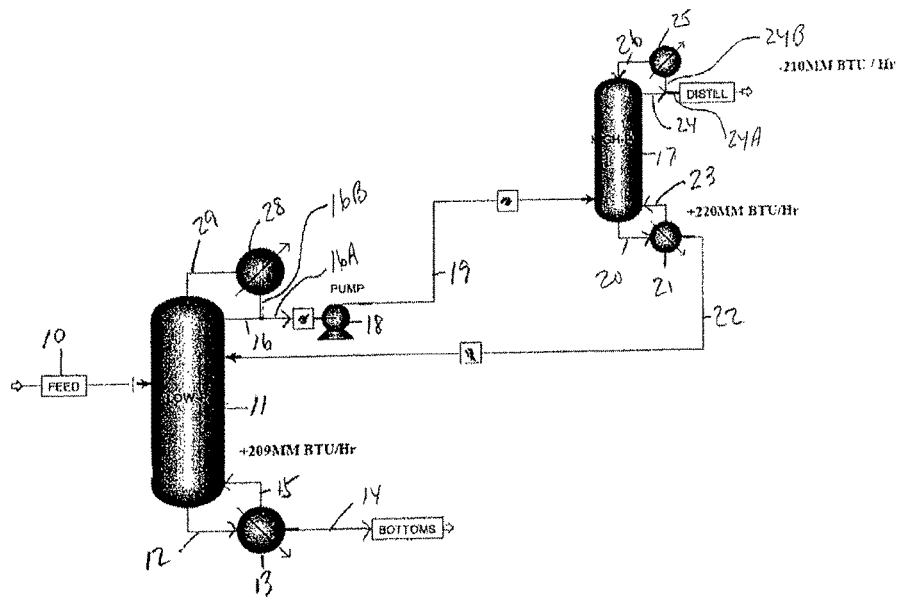
FIG. 1 is schematic of one embodiment of the process of this invention.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

"A", "an", "the", "at least one", and "one or more" are used interchangeably. The terms "comprises," "includes," and variations thereof do not have a limiting meaning where these terms appear in the description and claims. Thus, for example, an process stream that includes "an" azeotropic agent can be interpreted to mean that the process stream includes "one or more" azeotropic agents.

"Comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step, or procedure, excepting those that are not essential to operability. The term "consisting of" excludes any component, step, or procedure not specifically delineated or listed.

The recitations of numerical ranges by endpoints include all numbers subsumed in that range (e.g., 1 to 5 includes 1, 1.5, 2, 2.75, 3, 3.80, 4, 5, etc.). For the purposes of the invention, and consistent, with what one of ordinary skill in the art would understand, a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. The recitations of numerical ranges and/or numerical values, including such recitations in the claims, can also be read to include the term "about". In such instances the term "about" refers to numerical ranges and/or numerical values that are substantially the same as those recited.

"Azeotrope", "azeotrope mixture" and like terms mean a liquid mixture of two or more substances which behaves like a single substance in that the vapor produced by partial evaporation of the liquid mixture has the same composition as the liquid mixture, and the liquid mixture does not change in composition as it evaporates. Smith and Van Ness, *Introduction to Chemical Engineering Thermodynamics*, 3$^{rd}$ Ed., p. 312, McGraw-Hill Book Co. As used in the context of this disclosure, the term "azeotrope" includes "near azeotrope" as defined below.

"Near azeotrope", "tangent pinch" and like terms mean a liquid mixture of two or more substances in which the relative volatility of the components is so close as to make distillation impractical. This is generally considered to occur when the relative volatility between the components to be separated is below 1.10.

"Azeotrope agent" and like terms mean a substance that when added to an azeotrope mixture comprising first and second components will form a new azeotrope mixture with one of the first and second components. The new azeotrope mixture will have a boiling point different from the original azeotrope mixture such that the first and second components of the original azeotrope mixture can be separated by distillation, i.e., one of the first and second components will remain with the new azeotrope (either as a distillation overhead or bottom) while the other will separate from the original azeotrope as a distillation overhead or bottom (whatever is the opposite of the new azeotrope).

"Heat pump" and similar terms mean a device that provides heat energy from a source of heat or "heat sink" to a destination. Heat pumps are designed to move thermal energy opposite to the direction of spontaneous heat flow by absorbing heat from a cold space and releasing it to a warmer one. A heat pump uses some amount of external power to accomplish the work of transferring energy from the heat source to the heat sink.

MMA Process

The process for producing methyl methacrylate by an esterification reaction between methacrolein and methanol is not particularly limited, and may comprise any of a suitable gas phase or liquid phase or slurry phase reaction. How to carry out the reaction is also not particularly limited, and the reaction may be carried out in any of a continuous or batch manner. For example, there can be given a process comprising carrying out the reaction using a palladium-based catalyst in a liquid phase in a continuous manner. The oxidative esterification process is well known. See, e.g., U.S. Pat. Nos. 5,969,178; 6,107,515; 6,040,472; 5,892,102; 4,249,019 and 4,518,796.

Methanol/MMA Azeotrope

In one embodiment, the process for manufacturing MMA produces a MMA/methanol azeotrope that has a composition of 0.92 mole fraction of methanol in the vapor and liquid phases and boils at a temperature of 64.5° C. and a pressure of 1,013 millibar (101.35 kiloPascal).

Pressure Swing Distillation Process

FIG. 1 describes one embodiment of this invention. Equipment representations are made with Aspen software. Feed stream 10 comprising the effluent from a reactor in which oxygen, methacrolein and methanol were reacted to make methyl methacrylate, contains nominally 0.13 mole fraction water, 0.75 mole fraction methanol, 0.038 mole fraction methacrolein, and 0.085 mole fraction MMA, at a temperature of approximately 80° C. (but ranging from 30° C. to 100° C.) enters first (low pressure) distillation column 11 at or near its vertical midpoint. The column is operated at atmospheric pressure, at which the azeotrope between methanol and MMA will occur at the conditions described above, i.e., 0.92 mole fraction of methanol and 0.08 mole fraction of MMA. The overhead stream from the column 11 is taken out of the top of the column in a concentration far enough removed from the azeotrope such that separation is still practical. In the bottom of tower 11, essentially all of the methanol is removed (99.95% by weight in the example) from the incoming feed material. Column 11 distillate bottoms, or simply "bottoms", are removed through line 12, passed through reboiler (i.e., a heat exchanger) 13 in which the temperature of the bottoms is reduced to the condensing temperature at atmospheric pressure, or approximately 60° C. to 70° C., in the Example, and recovered through line 14. In one embodiment a side stream of the bottoms from column 11 is recycled from reboiler 13 through line 15 to the bottom of column 11 to assist in maintaining the desired operating temperature of column 11.

Reboiler 13 and lines 12, 14 and 15 are graphical representations of a conventional reboiler circuit. In practice, in a thermosyphon reboiler, liquid leaves the bottom of tower 11 in line 12 and enters reboiler 13. Part of the liquid is vaporized providing the heat to the tower required for the separation, and a part of the liquid is passed forward as product, i.e., bottoms, through line 14.

Distillate overheads, or simply "overheads", are removed from near the top of column 11 via line 16 and split into two streams by any conventional means, e.g., a forked or Y-pipe. The first stream of overheads from column 11 passes through line 16A to pump 18 and then through line 19 to second (high pressure) distillation column 17. The second stream of overheads from column 11 passes from line 16 through line 16B to condenser 28 from where it is recycled back to the top of column 11 through line 29.

In one embodiment distillation column 11 operates at a ratio of pressure to distillation column 17 of at least 1 to 5. In one embodiment column 11 operates at a pressure of 101.325 kilopascals of absolute pressure, where the azeotrope is present, column 17 operates at a pressure of 5 times that, or 506.625 kilopascals, where the azeotrope has been shifted because of the pressure difference.

The bottoms from column 17 are removed through line 20, passed through reboiler (i.e., a heat exchanger) 21, and recycled to the upper half of column 11 via line 22. In one embodiment a side stream of bottoms is recycled from reboiler 21 through line 23 to the bottom of column 17 to assist in maintaining the desired operating temperature of column 17.

In one embodiment the overheads from column 17 pass through line 24 and are split by any conventional means, e.g., a forked or Y-pipe, into lines 24A and 24B. The overheads in line 24A are collected as distillate product, and the overheads in line 24B are passed to condenser 25. In one embodiment the overheads from column 17 are recycled to the top of column 17 by line 26. The recycled overheads from column 17 assist in maintaining the desired operating temperatures of column 17.

Reboiler

In one embodiment the process of this invention transfers energy in the form of heat from high pressure column 17 to low pressure column 11. This transfer occurs by removing methanol from condenser 25 to reboiler 13 of low pressure column 11. This heat transfer reduces the duty required to operate the combined tower operation by 49% of the energy required without the combined heat integration. In the following example, 1.545e+08 watts are transferred from condenser 25 at the top of high pressure tower 17 to the low pressure column 11. Thus, the external energy input required to operate the low pressure column is reduced by this same amount. This, in essence, is a 50% reduction in the energy input requirements to the separation.

Although the invention has been described primarily in the context of a process for the manufacture of MMA, the invention has applicability in any circumstance in which an azeotrope of methanol and MMA is to be broken. While the practice of the invention does not require the use of an azeotropic agent, it allows for the use of such an agent if desired.

The invention is further described, but not limited, by the following numerical simulation example.

Example

The following is a numerical simulation (Aspen Version 8.0) demonstrating the removal of the MMA component from the overhead product of column 17 in FIG. 1 with only parts per million of methanol remaining in the bottom product of column 17. The heat can be transferred directly from the vapor leaving the top of column 17 and condensing on the shell or tube side of reboiler 13. This is the most thermodynamically efficient manner of transferring the heat since there is no entropy loss. For the sake of convenience, the vapor from the top of column 17 may be transferred and condensed to a working fluid, such as water or another convenient heat transfer fluid, and then transferred to reboiler 13.

TABLE 1

Numerical Simulation of Breaking a Methanol/MMA Azeotrope

|  | 10 FEED | 24A DISTILLATE | 14 BOTTOMS |
|---|---|---|---|
| Temperature ° C. | 80 | 110.5 | 77.9 |
| Pressure bar | 4.9 | 5 | 1 |
| Mass Frac |  |  |  |
| H2O | 0.06 | 293 PPM | 0.248 |
| MEOH | 0.623 | 0.822 | 0.001 |
| MAL | 0.069 | 0.091 | 105 PPB |
| MMA | 0.22 | 0.083 | 0.647 |
| Mole Frac |  |  |  |
| H2O | 0.128 | 585 PPM | 0.649 |
| MEOH | 0.741 | 0.921 | 0.002 |
| MAL | 0.038 | 0.047 | 71 PPB |
| MMA | 0.084 | 0.03 | 0.305 |
| Mole Flow kmol/h |  |  |  |
| H2O | 265.645 | 0.977 | 264.637 |
| MEOH | 1540.043 | 1539.324 | 0.85 |
| MAL | 78.226 | 78.224 | <0.001 |
| MMA | 174.108 | 49.804 | 124.28 |

$H_2O$-Water
MeOH-Methanol
MAL-Methacrolein
MMA-Methyl Methacrylate
PPM-Parts per million
Frac-Fraction
Kmol/h-kilomoles per hour In FIG. 1 and the numerical information of Table 1, the main entrance and exit streams to separation columns 11 and 17 are shown. Feed stream 10 enters column 11 from the upstream reactor. It contains unreacted methanol, water produced in the stoichiometry, and the MMA produced in the reaction, along with some unreacted MAL. This feed is introduced to low pressure column 11 where below the feed point, stripping of the light keys and anything lighter than the light key takes place. Essentially all of the methanol is removed from the feed, and the bottoms stream exits low pressure column 11 through line 14 free of methanol. The upper section of the low pressure column, the rectification section, enriches the material in methanol past the point that the azeotrope that exists at lower pressure would allow. The material is condensed in condenser 28, and part is returned as reflux to column 11 through line 16. The other part is pumped to high pressure tower 17.

Figure 2:
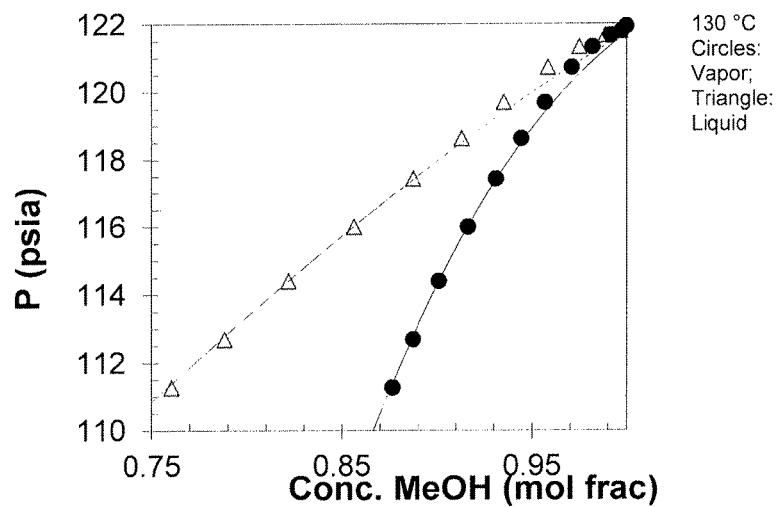
FIG. 2 is a graph reporting the concentration of methanol in the vapor and liquid phases at an elevated pressure and temperature of a binary mixture of methanol and MMA, demonstrating that a separation is achievable at an elevated pressure and temperature.
Figure 3:
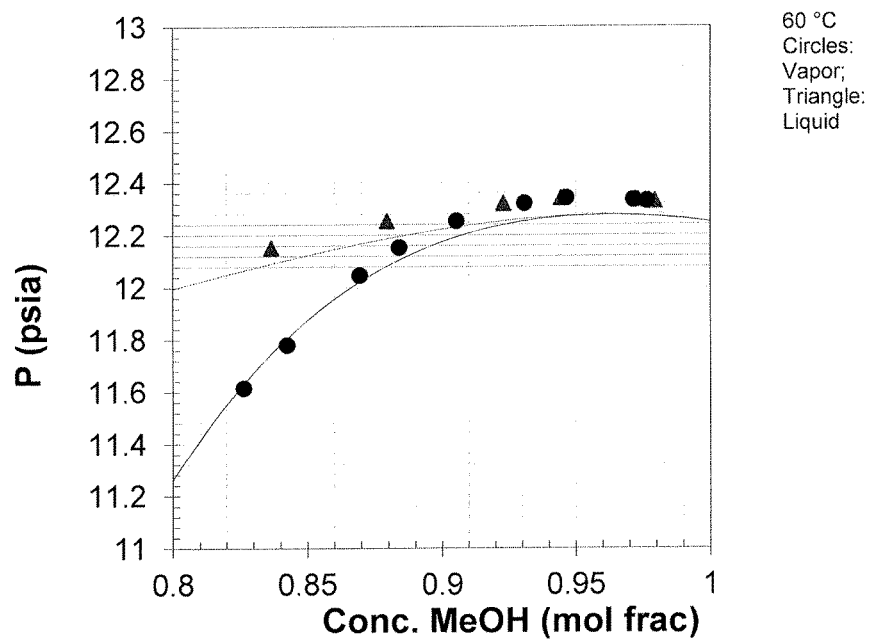
FIG. 3 is a graph reporting the concentration of methanol in the vapor and liquid phases at a lower pressure and temperature of a binary mixture of methanol and MMA, demonstrating that a separation is not achievable at a lower pressure and temperature since the vapor and liquid compositions are essentially identical.

As seen in FIG. 2 and FIG. 3, the azeotrope between methanol and MMA is shifted by the increase in pressure. Thus, the enrichment of methanol can proceed by rectification at the higher pressure.

While the azeotrope can be shifted by higher pressure, the relative volatility between methanol and MMA is still between 1.2 and 1.4 at a pressure of 500 kilopascals, requiring that a relatively high reflux ratio be used to rectify the remainder of the methanol. This results in a high energy consumption without the addition of the integration to utilize the heat from the high pressure column to the low pressure column.

What is claimed is:

1. A process for breaking or minimizing a methanol/methyl methacrylate (MMA) azeotrope, the process comprising the steps of:
   (A) feeding a liquid stream comprising methanol and MMA to a first distillation column operated at a first pressure and equipped with a reboiler;
   (B) separating the liquid stream within the first distillation column into a first distillation column overheads stream comprising a methanol/MMA azeotrope and a first distillation column bottoms stream;
   (C) transferring the first distillation column overheads stream to a second distillation column operated at a second pressure, the operating pressure of the second distillation column greater than the operating pressure of the first distillation column;
   (D) separating the first distillation column overheads stream within the second distillation column into a second distillation column overheads stream comprising an amount of methanol/MMA azeotrope that is less than the amount of methanol/MMA azeotrope in the first column overheads stream, and a second distillation column bottoms stream; and
   (E) recovering at least a part of the second distillation column overheads stream.

2. The process of claim 1 further comprising the step of transferring heat from the second distillation column to the first distillation column by recycling at least a part of the second distillation column overheads stream to the reboiler of the first distillation column.

3. The process of claim 1 in which the methanol/MMA azeotrope is within a product stream of an MMA manufacturing process in which methacrolein and methanol are reacted.

4. The process of claim 1 in which the first distillation column operates at a ratio of pressure to the second distillation column of at least 1 to 5.

5. The process of claim 1 in which an azeotropic agent is not used.

6. The process of claim 1 in which an azeotropic agent is present in the second distillation column.

* * * * *